United States Patent
Junio et al.

(10) Patent No.: US 12,213,744 B2
(45) Date of Patent: Feb. 4, 2025

(54) PATH PLANNING BASED ON WORK VOLUME MAPPING

(71) Applicant: Mazor Robotics Ltd., Caesarea (IL)

(72) Inventors: Dany Junio, Tel Aviv-Jaffa (IL); Moshe Shoham, Hoshaya (IL)

(73) Assignee: Mazor Robotics Ltd., Caesarea (IL)

( * ) Notice: Subject to any disclaimer, the term of this patent is extended or adjusted under 35 U.S.C. 154(b) by 565 days.

(21) Appl. No.: 17/376,493

(22) Filed: Jul. 15, 2021

(65) Prior Publication Data
US 2023/0020476 A1    Jan. 19, 2023

(51) Int. Cl.
*A61B 34/30* (2016.01)
*A61B 17/02* (2006.01)
*A61B 34/20* (2016.01)

(52) U.S. Cl.
CPC .......... *A61B 34/20* (2016.02); *A61B 17/0218* (2013.01); *A61B 34/30* (2016.02); *A61B 2034/2051* (2016.02); *A61B 2034/2055* (2016.02)

(58) Field of Classification Search
CPC ..... A61B 34/20; A61B 17/0218; A61B 34/30; A61B 2034/2051; A61B 2034/2055
See application file for complete search history.

(56) References Cited

U.S. PATENT DOCUMENTS

| 9,265,587 | B2 | 2/2016 | Vancamberg et al. |
| 9,734,632 | B2 | 8/2017 | Thomas et al. |
| 2014/0276943 | A1 | 9/2014 | Bowling et al. |
| 2017/0333137 | A1 | 11/2017 | Roessler |
| 2019/0262084 | A1* | 8/2019 | Roh ........................ G16H 20/40 |
| 2020/0086437 | A1* | 3/2020 | Johnson ................. B25J 9/1664 |

FOREIGN PATENT DOCUMENTS

| CN | 105455901 | 2/2018 |
| WO | WO 2020/236937 | 11/2020 |

OTHER PUBLICATIONS

International Search Report and Written Opinion for International (PCT) Patent Application No. PCT/IL2022/050742, dated Oct. 21, 2022, 16 pages.

* cited by examiner

*Primary Examiner* — Rochelle D Turchen (74) *Attorney, Agent, or Firm* — Sheridan Ross P.C.

(57) ABSTRACT

Systems, methods, and devices for planning a path are provided. A work volume and one or more no-fly zones may be mapped. The work volume may define a volume in which a robot may access and each of the one or more no-fly zones may define at least one volume in which a robot is restricted from accessing. Information may be received about a position of at least one instrument and a void volume may be calculated based on the position of the at least one instrument. The work volume may be updated to include the void volume to yield an updated work volume. A path may be calculated for a robotic arm of a robot from outside a patient anatomy to within the patient anatomy that is within the updated work volume and avoids the one or more no-fly zones.

16 Claims, 3 Drawing Sheets

PATH PLANNING BASED ON WORK VOLUME MAPPING

FIELD

The present technology generally relates to path planning, and relates more particularly to path planning based on mapped work volumes and no fly zones.

BACKGROUND

Surgical robots may assist a surgeon or other medical provider in carrying out a surgical procedure, or may complete one or more surgical procedures autonomously. The surgical robots may be configured to orient an end effector and/or a tool during the surgical procedure.

SUMMARY

Example aspects of the present disclosure include:

A method for planning a path according to at least one embodiment of the present disclosure comprises mapping a work volume and one or more no-fly zones, the work volume defining a volume in which a robot may access and each of the one or more no-fly zones defining at least one volume in which a robot is restricted from accessing; receiving information about a position of at least one instrument; calculating a void volume based on the position of the at least one instrument; updating the work volume to include the void volume to yield an updated work volume; and calculating a path for a robotic arm of a robot from outside a patient anatomy to within the patient anatomy that is within the updated work volume and avoids the one or more no-fly zones.

Any of the aspects herein, wherein the information about the position of the at least one instrument is received from at least one of a navigation camera, an electro-magnetic navigation system, or a Lidar navigation system.

Any of the aspects herein, wherein the at least one instrument is a retractor.

Any of the aspects herein, wherein the at least one instrument is at least one of a port and a tubular retractor.

Any of the aspects herein, wherein determining the void volume is further based on known dimensions of the at least one instrument.

Any of the aspects herein, wherein a void that defines the void volume comprises an incision.

Any of the aspects herein, further comprising: receiving information about a surgical operating room, wherein the information is at least one of an image, sensor data, electro-magnetic data, or Lidar data; identifying one or more obstacles in the image; and defining the one or more no-fly zones based on the identified one or more obstacles.

Any of the aspects herein, wherein defining the one or more no-fly zones comprises determining an outer boundary of one or more objects.

Any of the aspects herein, wherein calculating the path is further based on one or more parameters and wherein the method further comprises assigning a weight to each parameter of the one or more parameters.

Any of the aspects herein, wherein artificial intelligence uses one or more data models to assign the weight.

Any of the aspects herein, further comprising: receiving updated information about an updated position of the at least one instrument; calculating at least one of an updated void volume and an updated position of the void volume based on the updated position of the at least one instrument; and updating the updated work volume based on at least one of the updated void volume and the updated position of the void volume.

Any of the aspects herein, further comprising: causing the robotic arm to move along the path.

Any of the aspects herein, further comprising: determining a cut angle to a target anatomical element based on avoiding the one or more no-fly zones, wherein calculating the path is further based on the determined cut angle.

Any of the aspects herein, wherein the one or more no-fly zone includes the at least one instrument.

A device for planning a path according to at least one embodiment of the present disclosure comprises at least one processor; and a memory storing data for processing by the at least one processor that, when processed, the data causes the at least one processor to: map a work volume and one or more no-fly zones, the work volume defining a volume in which a robot may access and each of the one or more no-fly zones defining at least one volume in which a robot is restricted from accessing; receive information about a position of at least one instrument and dimensions of an incision; calculate a void volume based on the position of the at least one instrument and the dimensions of the incision; update the one or more no-fly zones to remove the void volume; and calculate a path for a robotic arm of a robot from outside a patient anatomy to within the patient anatomy that avoids the one or more no-fly zones.

Any of the aspects herein, wherein one or more markers are affixed to the at least one instrument and the information about the position of the at least one instrument is received from a navigation camera configured to detect the position of the one or more markers.

Any of the aspects herein, wherein the memory stores further data for processing by the processor that, when processed, causes the processor to: receive an image of the incision; and determine the dimensions of the incision from the image.

Any of the aspects herein, wherein the memory stores further data for processing by the processor that, when processed, causes the processor to: receive updated information about an updated position of the at least one instrument; calculate at least one of an updated void volume and an updated position of the void volume based on the updated position of the at least one instrument; and update the updated work volume based on at least one of the updated void volume and the updated position of the void volume.

Any of the aspects herein, wherein determining the void volume is further based on known dimensions of the at least one instrument.

A system for orienting a robotic arm according to at least one embodiment of the present disclosure comprises a robotic arm; at least one processor; and a memory storing data for processing by the at least one processor that, when processed, the data causes the at least one processor to: map a work volume and one or more no-fly zones, the work volume defining a volume in which a robot may access and each of the one or more no-fly zones defining at least one volume in which a robot is restricted from accessing; receive information about a position of at least one instrument; calculate a void volume based on the position of the at least one instrument; update the work volume to include the void volume to yield an updated work volume; calculate a path for a robotic arm of a robot from outside a patient anatomy to within the patient anatomy based on the updated work volume and that avoids the one or more no-fly zones; and cause the robotic arm to move along the path.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

When performing a surgical procedure or task using a fully autonomous robot within a patient's anatomy, such as bone cutting or drilling, path planning for such procedure or task may account for additional considerations. For example, the additional considerations may include accounting for a robot that may hover outside of a "no-fly" zone during insertion of surgical tools by a surgeon or assistant.

In a fully autonomous procedure, the path for the robot may be much more complex. While the initial motion to an approximate location of a patient's anatomy may be performed using a "no-fly" zone and the last part of the path or motion, which is the actual bone cutting, could be performed knowing that the tooltip will necessarily collide with the patient's anatomy or cut that specific section of the spine, the motion in-between the two motions may be more complex. The motion in-between may include initial, far away position of the robot hovering above the "no-fly" zone to the actual cutting motion. In this motion in-between, bony anatomy, screw towers, screw tulips, or other major soft tissue still there, are to be avoided. While in this step, the active cutting tool may be turned off.

In at least one embodiment of the present disclosure, different parameters to be used as baseline considerations for a "mid-motion" path planning may be combined using one or more of the following parameters:
(1) Existing screws detected from, for example, a CT or MM scan may be accounted for in the path planning. Screws placed during a procedure (either assuming they are in position or saving a location of the screws using a navigation system) may also be accounted for in the path planning.
(2) Towers placed during a procedure (either assuming they are in position or saving a location of the screws using a navigation system) may also be accounted for in the path planning.
(3) Bony anatomy, which may be detected in, for example, an image, may be accounted for. The bone may be considered to ensure that the path does not collide with the bone.
(4) Soft-tissue information based on, for example, and MM may be accounted for in the path planning. For example, organs may be considered to ensure that the path does not collide with the organs.
(5) An existing incision may be accounted for in the path planning. For example, utilizing 3D mapping capability (or other similar functionality), a boundary of the incision may be detected and used in consideration to minimize a width of the incision when accessing a desired path.
(6) A bone cut angle may be accounted for in the path planning. More specifically, the bone cut direction itself may be considered such that an amount of motion that a cutting tool needs to perform within the "no-fly" zone is minimized.

A software may perform a calculation of the "mid"-path planning given the above considerations in order to optimize the path per weighting of the different parameters. The parameter may be weighted using parametric weighting, machine learning, artificial intelligent, or other methods.

The present disclosure provides a fundamental block that will support a procedure where a robot performs a procedure, such as, for example, a cut autonomously and can move to and from the cut autonomously (without removing the cutting tool between each cut).

Embodiments of the present disclosure provide technical solutions to one or more of the problems of (1) autonomous robotic movement, (2) path planning for an autonomous robotic arm, (3), defining a work volume (4) increasing patient safety.

Figure 1:
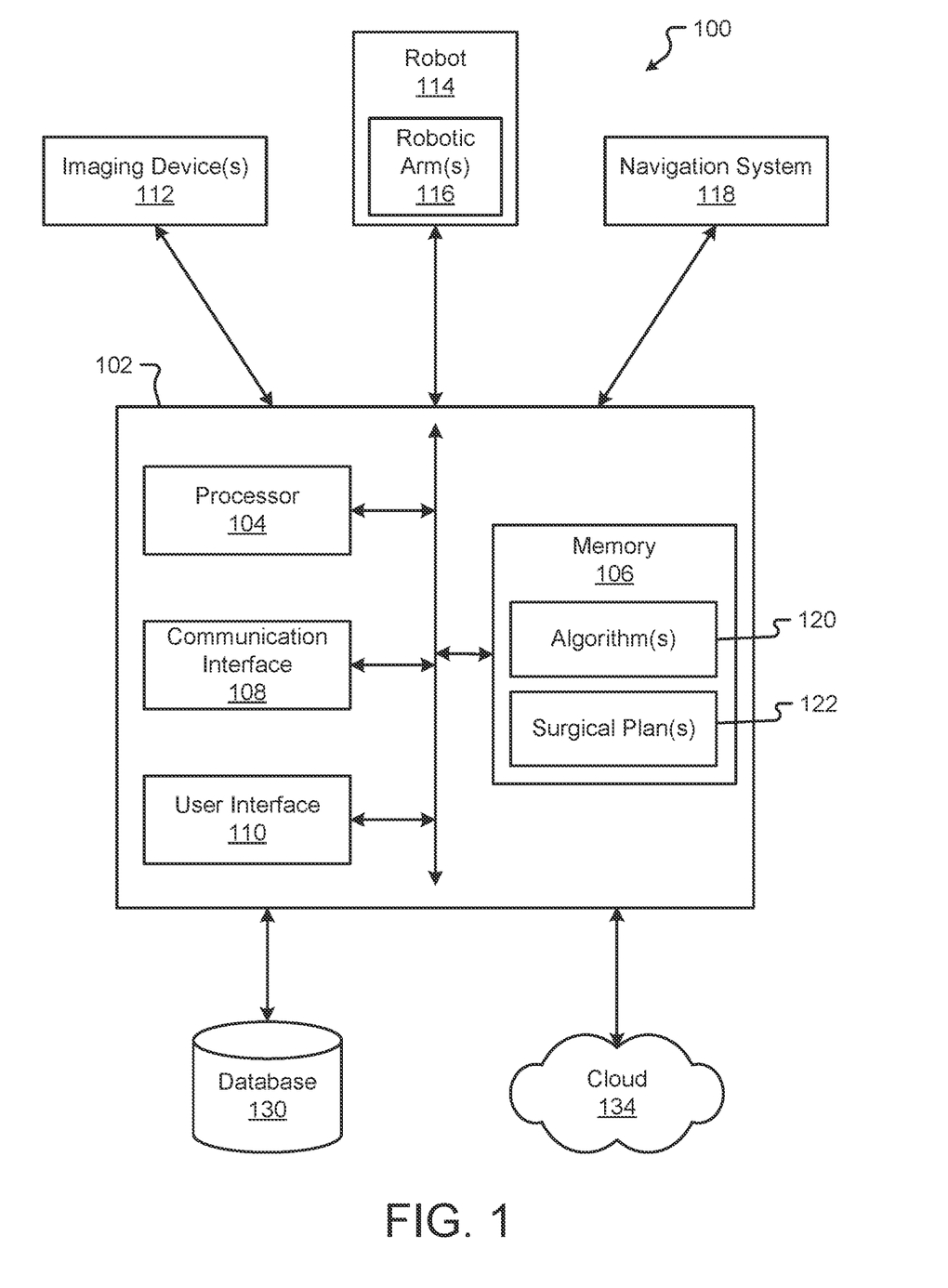
FIG. 1 is a block diagram of a system according to at least one embodiment of the present disclosure.

Turning first to FIG. 1, a block diagram of a system 100 according to at least one embodiment of the present disclosure is shown. The system 100 may be used to plan a path for a robotic arm and/or carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 200 and/or 300 described herein, or of any other methods. The memory 106 may store, for example, one or more algorithms 120 and/or one or more surgical plans 122. Such algorithms may, in some embodiments, be organized into one or more applications, modules, packages, layers, or engines. Alternatively or additionally, the memory 106 may store other types of data (e.g., machine learning modes, artificial neural networks, etc.) that can be processed by the processor 104 to carry out the various method and features described herein. Although various components of memory 106 are described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, and/or the cloud 134.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image one or more objects (e.g., tools, instruments, components, etc.), anatomical feature(s) (e.g., a bone, veins, tissue, etc.) and/or other aspects of patient anatomy to yield image data (e.g., image data depicting or corresponding to a bone, veins, tissue, objects, tool, instruments, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure.

In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, a depth camera, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MM) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient or one or more objects. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or comprise, for example, the Mazor X™ Stealth Edition robotic guidance system. The robot 114 may be configured to position a tool at one or more precise position(s) and orientation(s), and/or to return the tool to the same position(s) and orientation(s) at a later point in time. The robot 114 may additionally or alternatively be configured to manipulate an imaging device such as the imaging device 112 (whether based on guidance from the navigation system 118 or not) to accomplish or to assist with a surgical task. In some embodiments, the robot 114 may be configured to hold and/or manipulate an anatomical element during or in connection with a surgical procedure.

The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the tool, the imaging device 112, and/or the anatomical element. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (i.e., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, depth cameras, infrared cameras, or other cameras. In some embodiments, the navigation system may comprise one or more electromagnetic sensors. In various embodiments, the navigation system 118 may be used to track a position and orientation (i.e., pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan such as the surgical plan 122.

The database 130 may store information that correlates one coordinate system to another (e.g., one or more robotic coordinate systems to a patient coordinate system and/or to a navigation coordinate system). The database 130 may additionally or alternatively store, for example, one or more surgical plans 122 (including, for example, pose information about a target and/or image information about a patient's anatomy at and/or proximate the surgical site, for use by the robot 114, the navigation system 118, and/or a user of the computing device 102 or of the system 100); one or more images useful in connection with a surgery to be completed by or with the assistance of one or more other components of the system 100; and/or any other useful information. The database 130 may be configured to provide any such information to the computing device 102 or to any other device of the system 100 or external to the system 100, whether directly or via the cloud 134. In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

The system 100 or similar systems may be used, for example, to carry out one or more aspects of any of the methods 200 and/or 300, described herein. The system 100 or similar systems may also be used for other purposes.

Figure 2:
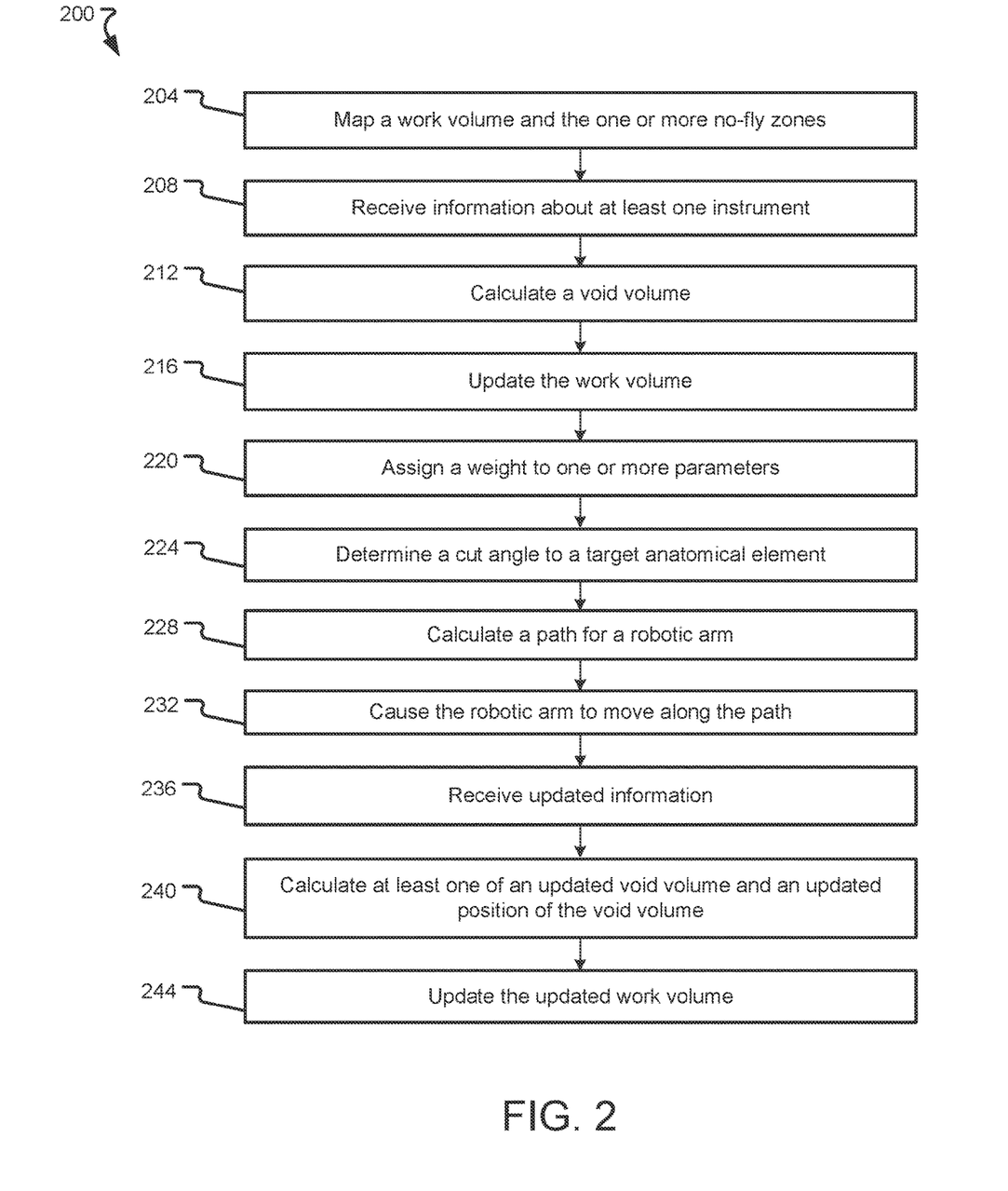
FIG. 2 is a flowchart according to at least one embodiment of the present disclosure.

FIG. 2 depicts a method 200 that may be used, for example, for planning a path for a robotic arm.

The method 200 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 200. The at least one processor may perform the method 200 by executing instructions stored in a memory such as the memory 106. The instructions may correspond to one or more steps of the method 200 described below. The instructions may cause the processor to execute one or more algorithms, such as the algorithm 120.

The method 200 comprises mapping a work volume and one or more no-fly zones (step 204). The work volume defines a volume of space surrounding a patient in which the robotic arm may access. Each of the one or more no-fly zones may define at least one volume in which a robotic arm such as the robotic arm 116 and/or any portion of a robot such as the robotic 114 is restricted from accessing. In other words, the robotic arm may be capable of accessing the at least one volume, but is prevented from doing so by, for example, control signaling. In such instances, the robotic arm and/or any portion of the robot may be stopped at a boundary of each of the one or more no-fly zones using control signaling. The control signaling may, for example, cause one or more motors to stop movement of the robotic arm and/or the robot at the boundary of a no-fly zone. The control signaling may also the one or more motors to move the robotic arm and/or the robot away from the boundary of the no-fly zone. In other examples, the control signaling may cause a brake to apply a braking force to the one or more motors to prevent movement of the robotic arm and/or the robot into the one or more no-fly zones.

Figure 3:
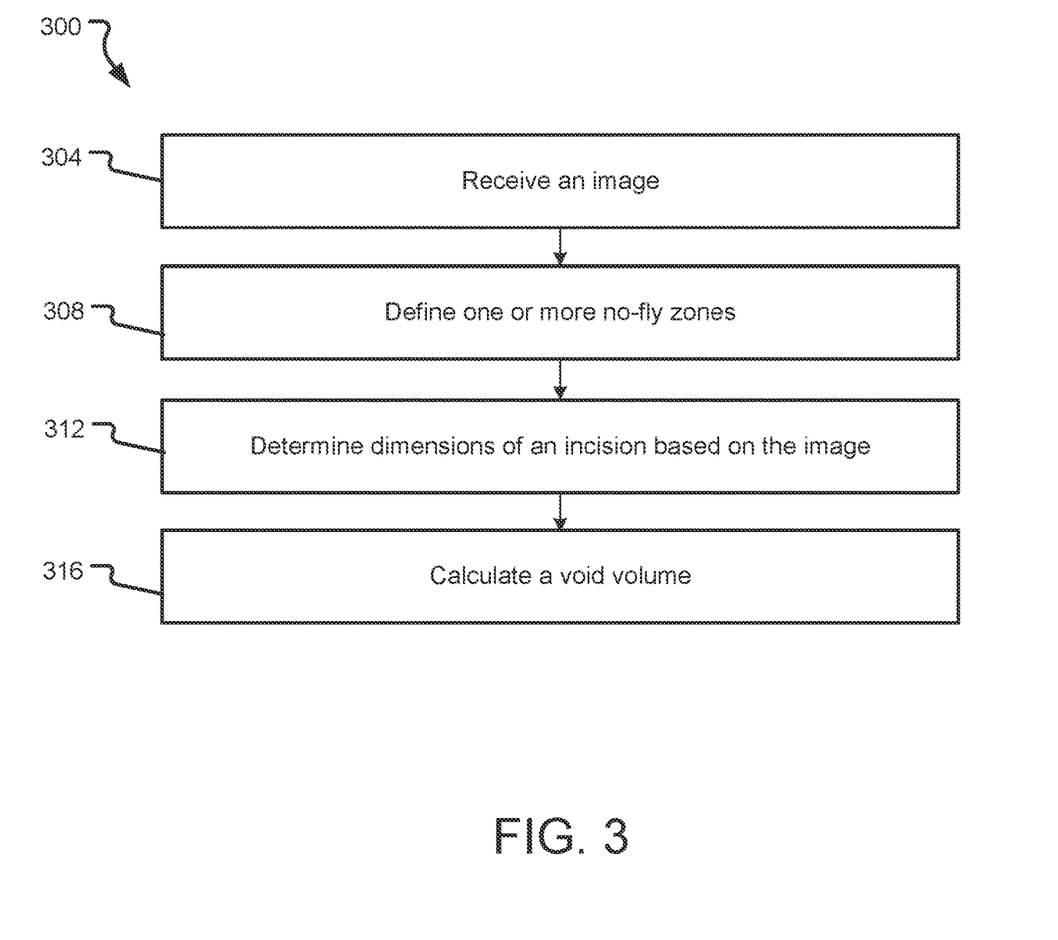
FIG. 3 is a flowchart according to at least one embodiment of the present disclosure.

In some embodiments, the work volume may be defined by defining a volume of the operating room and subtracting the one or more no-fly zones from the volume. The volume of the operating room may be determined by, for example, a processor such as the processor 104 based on information about the operating room. The information may be, for example, an image, sensor data, Lidar data, and/or electromagnetic data. In other instances, the volume of the operating room may be calculated from dimensions of the room. The one or more no-fly zones may be determined in step 308 of method 300, described below.

The work volume may be mapped automatically by a processor such as the processor 104. In some embodiments, a 3D model may be generated based on the work volume. In other embodiments, the work volume may be or comprise, or be based on, surgeon input received via a user interface such as the user interface 110. In further embodiments, the work volume may be mapped automatically by the processor, and may thereafter be reviewed and approved (or modified) by a surgeon or other user.

The method 200 also comprises receiving information about at least one instrument (step 208). The at least one instrument may be any instrument such as, for example, a retractor, a tubular retractor, or a port.

In some embodiments, information about the at least one instrument may comprise position data. In some embodiments, the position data may be received from a sensor, such as a position sensor. In other embodiments, the position data may be received from a navigation camera of a navigation system such as the navigation system 118. In such embodiments, the at least one instrument may include a reference marker detectable by the navigation system. In other embodiments, the position data may be received from a robotic arm such as the robotic arm 116 orienting or supporting the at least one instrument. In still other embodiments, the position data may be received as input from a user such as, for example, a surgeon.

In other embodiments, the information may comprise dimensions regarding the at least one instrument. The dimensions may be dimensions of the at least one instrument. For example, the dimensions may include a width, a length, a depth, a thickness, and/or a diameter of the at least one instrument. The dimensions may also include relative dimensions of the at least one instrument. For example, the dimensions may include a distance between two components of at least one instrument, such as, for example, a distance between two arms of a retractor. In some embodiments, the dimensions may be received as input from the user. In other embodiments, the dimensions may be received from a database such as the database 130. In still other embodiments, the dimensions may be measured preoperatively or intraoperatively by, for example, the user or the navigation system.

The method 200 also comprises calculating a void volume (step 212). The void volume may be calculated based on at least the position of the at least one instrument. In some embodiments, the void volume may be calculated based on the dimensions of the at least one instrument. In other embodiments, the void volume may be calculated based on dimensions of the void volume as determined by, for example, an imaging device such as the imaging device 112, as will be described in more detail with respect to method 300.

In some embodiments, the void volume corresponds to a volume of space residing in or proximate to an incision recently made in a patient during the surgical procedure. In such embodiments, the void volume may be calculated in real-time during a surgical procedure by calculating a volume of an opening created by the at least one instrument in the patient. In examples where the at least one instrument is a retractor, the void volume may be calculated based on a depth of the retractor in the patient and a distance between each arm of the retractor. In examples where the at least one instrument is a port, the void volume may be calculated based on a depth of the port within the patient and a diameter of the port. In examples where the at least one instrument is a tubular retractor, the void volume may be calculated based on a depth of the tubular retractor within the patient and a diameter of the tubular retractor.

The method 200 also comprises updating the work volume (step 216). In some embodiments, updating the work volume may comprise adding the void volume to the work volume by, for example, the processor. In embodiments where the work volume is represented by a 3D model, the void volume may be rendered and added to the 3D model. In other embodiments, updating the work volume may comprise removing the void volume from the one or more no-fly zones by, for example, the processor. Updating the work volume yields an updated work volume.

The method 200 also comprises assigning a weight to one or more parameters (step 220). The one or more parameters may be used when calculating a path for a robotic arm such as the robotic arm 116 in step 228 described below. The one or more parameters may be obtained from a surgical plan such as the surgical plan 122 or as input from a user such as, for example, a surgeon or medical provider. In some embodiments, the one or more parameters may be based on historical data or cases.

The one or more parameters may be, for example, existing tools in or positioned on a patient (e.g., spinal screws and/or towers), boney anatomy, soft-tissue, existing or prior incisions, or bone cut angle. In some embodiments, the one or more parameters are assigned a weight based on user input. In other embodiments, artificial intelligence may use one or more data models to assign the weight. The one or more data models may be trained using one or more training data sets. The training data sets may comprise, for example, historical data (such as, historical parameters, for example), surgical plans (whether past or present, or both), user preference (e.g., a surgeon's preference), and/or images (whether 3D or 2D, or both) of the instruments and/or patients.

The method 200 also comprises determining a cut angle to a target anatomical element (step 224). Determining the cut angle to the target anatomical element may be based on, for example, the work volume and the one or more no-fly zones mapped in step 208 and the void volume calculated in step 216. The cut angle may be based on orienting a tool or an instrument such that the tool or instrument avoids the one or more no-fly zones when disposed at the cut angle and when being positioned at the cut angle. In some embodiments, the target anatomical element may be a vertebra. In such embodiments, the tool or instrument may be a spinal screw and a cut angle of the spinal screw to the vertebra may be based on avoiding the one or more no-fly zones when orienting the spinal screw to the vertebra. In other embodiments, the tool or instrument may be any tool or instrument used during a surgical procedure.

The method 200 also comprises calculating a path for a robotic arm (step 228). The path may extend from outside of a patient anatomy to within the patient anatomy. The path is also disposed within the updated work volume and avoids the one or more no-fly zones. The path may also ensure that any portion of the robot avoids the one or more no-fly zones. In some embodiments, the path may be further based on the one or more parameters (whether assigned a weight or not) described in step 224. In other embodiments, the path may be further based on the cut angle determined in step 228. It will be appreciated that the path may simply be based on the updated work volume and the one or more no-fly zones.

The method 200 also comprises causing the robotic arm to move along the path (step 232). In some embodiments, instructions to cause the robotic arm to move along the path may be generating by, for example, the processor and transmitted to the robotic arm (or a controller thereof). In other embodiments, instructions to orient the robotic arm at one or more poses may be generated by, for example, the processor and displayed on a user interface such as the user interface 110.

The method 200 comprises receiving updated information about the at least one instrument (step 236). The step 234 may be the same as or similar to the step 208 described above. In some embodiments, the updated information includes an updated position of the at least one instrument. In other embodiments, the updated information includes an updated dimension of the at least one instrument. For example, a width between retractor arms may increase or decreased when the retractor arms are moved.

The method 200 also comprises calculating at least one of an updated void volume and an updated position of the void volume (step 240). The step 238 may be the same as or similar to the step 212 with respect to calculating an updated void volume. The updated position of the void volume may be based on the updated position of the at least one instrument. For example, a port may be moved to a new position and thus, the updated position of the void volume may correspond to the new position of the port.

The method 200 also comprises updating the updated work volume (step 244). The step 242 may be the same as or similar to the step 216, described above. Updating the updated work volume may be based on the updated void volume and/or the updated position of the void volume calculated from step 238. In some embodiments, the initial void volume may be deleted or removed (from a 3D model, for example) prior to updating the updated work volume with the updated void volume.

It will be appreciated that the steps 236244 may be repeated. For example, the steps 236-244 may be repeated anytime the at least one instrument is moved and/or adjusted. In another example, the steps 236-244 may be repeated when an additional instrument is inserted into a patient to calculate an additional void volume based on the additional instrument. In still another example, the steps 236-244 may be repeated when an initial instrument is replaced with a new instrument, and thus, a new void volume may be calculated based on the new instrument.

It will also be appreciated that steps 228 and 232 may be repeated after steps 236-244. In other words, the path for a robotic arm may be recalculated via step 228 based on the subsequent updated work volume updated in step 244.

The present disclosure encompasses embodiments of the method 200 that comprise more or fewer steps than those described above, and/or one or more steps that are different than the steps described above.

FIG. 3 depicts a method 300 that may be used, for example, for calculating a void volume.

The method 300 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 300. The at least one processor may perform the method 300 by executing instructions stored in a memory such as the memory 106. The instructions may correspond to one or more steps of the method 300 described below. The instructions may cause the processor to execute one or more algorithms, such as the algorithm 120.

The method 300 comprises receiving an image (step 304). The image may be received or obtained from an imaging device such as the imaging device 112, which may be any imaging device such as a camera, a depth camera, X-ray based imaging device, or ultrasound imaging device. The image may comprise one or more 2D images, one or more 3D images, or a combination of one or more 2D images and one or more 3D images. In some embodiments, one imaging device may be used to obtain the image. In other embodiments, multiple imaging devices may be used to obtain the image. In examples wherein more than one image is received or multiple images are used to construct a 3D model, a first imaging device may obtain a first one of the images independently of a second imaging device obtaining a second one of the images. In another example, at least a first one of the images may be obtained with a first imaging device and at least a second one of the images may be obtained with a second imaging device. In other embodiments, the image may be received via a user interface such as the user interface 110 and/or via a communication interface such as the communication interface 108 of a computing device such as the computing device 102, and may be stored in a memory such as the memory 106. The image may also be generated by and/or uploaded to any other component of the system 100. In some embodiments, the image may be indirectly received via any other component of the system 100 or a node of a network to which the system 100 is connected.

The image may depict one or more objects and/or reference markers affixed to the one or more objects of a surgical operating room. The image may also depict an incision of a patient. The image may be processed using an image processing algorithm to identify the one or more objects and/or the incision. In some embodiments, feature recognition may be used to identify a feature of the one or more objects. For example, a tool or instrument may be identified in the image. In other embodiments, the image processing algorithm may be based on artificial intelligence or machine learning. In such embodiments, a plurality of training images may be provided to a processor such as the processor 104, and each training image may be annotated to include identifying information about an object or an incision in the image. The processor, executing instructions stored in memory such as the memory 106 or in another memory, may analyze the images using a machine-learning algorithm and, based on the analysis, generate one or more image processing algorithms for identifying objects or an incision in an image. Such image processing algorithms may then be applied to the image received in step 304, as described above.

The method 300 comprises defining one or more no-fly zones (step 308). Each of the one or more no-fly zones define at least one volume in which a robotic arm such as the robotic arm 116 and/or any portion of a robot such as the robot 114 is restricted from accessing. In some embodiments, the one or more no-fly zones may be defined automatically using artificial intelligence and a model trained using training data (e.g., historical cases). In other embodiments, the one or more no-fly zones may be or comprise, or be based on, surgeon input received via the user interface. In further embodiments, the one or more no-fly zones may be defined automatically using artificial intelligence, and may thereafter be reviewed and approved (or modified) by a surgeon or other user.

More specifically, the one or more no-fly zones may be based on one or more objects identified in a surgical operating room. The one or more objects may be, for example, instruments, tools, equipment, fixtures, a patient, or any component for a surgical procedure. The one or more objects may be external or internal to the patient. The one or more objects may be identified, for example, by a navigation system such as the navigation system 118. In other embodiments, an imaging device such as the imaging device 112 may obtain an image of the operating room and a processor such as the processor 104 may identify one or more objects in the image, as described above with respect to step 304.

The one or more no-fly zones may be defined by the outer boundary of each of the one or more objects. Based on the image, an outer boundary of the one or more objects may be determined by, for example, the processor or a user. In embodiments where the one or more objects are identified by the navigation system, the outer boundary of each object may be determined based on the markers affixed to the object. In other instances, the outer boundary may be determined using known dimensions of each object and the position of each object as determined by the navigation system.

The method 300 also comprises determining dimensions of an incision based on the image (step 312). The image may be received in step 304, described above. The image may be processed by, for example, the processor using the image processing algorithm to identify the incision. The processor may also use the image processing algorithm to identify a boundary of the incision using, for example, feature recognition. The processor may also determine a width, a length, a depth, and/or a volume of the incision based on, for example, the identified boundary.

The method 300 also comprises calculating a void volume (step 316). The step 316 may be the same as or similar to the step 212 of method 200, described above. Further, calculating the void volume may be based on the dimensions of the incision determined in step 312, described above.

It will be appreciated that the method 300 may be used in conjunction with the method 200. For example, step 308 regarding defining the one or more no-fly zones may occur prior to step 204 regarding mapping the work volume and the one or more no-fly zones. In another example, step 312 regarding determining dimensions of an incision based on an image may be used by step 228 to calculate the path for the robotic arm. It will also be appreciated that the steps 304-316 may be repeated. For example, the steps 304-316 may be repeated when a new instrument is inserted. In another example, the steps 304-316 may be repeated with the at least one instrument is repositioned or adjusted (for example, if retractor arms are adjusted). In still another example, the steps 304-316 may be repeated when the at least one instrument is replaced with a new instrument.

The present disclosure encompasses embodiments of the method 300 that comprise more or fewer steps than those described above, and/or one or more steps that are different than the steps described above.

As noted above, the present disclosure encompasses methods with fewer than all of the steps identified in FIGS. 2 and 3 (and the corresponding description of the methods 200 and 300), as well as methods that include additional steps beyond those identified in FIGS. 2 and 3 (and the corresponding description of the methods 200 and 300). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:
1. A method for planning a path comprising:
mapping a work volume and one or more no-fly zones, the work volume defining a volume which a robot may access and each of the one or more no-fly zones defining at least one volume which the robot is restricted from accessing;
receiving information about a position of at least one instrument;
receiving an image of an incision;
processing the image to determine dimensions of the incision based on the image;

calculating a void volume based on the position of the at least one instrument and the dimensions of the incision;
updating the work volume to include the void volume to yield an updated work volume; and
calculating a path for a robotic arm of the robot from outside a patient anatomy to within the patient anatomy that is within the updated work volume and avoids the one or more no-fly zones,
wherein calculating the void volume is further based on known dimensions of the at least one instrument obtained from measurements of the at least one instrument received from a database.

2. The method of claim 1, wherein the information about the position of the at least one instrument is received from at least one of a navigation camera, an electro-magnetic navigation system, or a Lidar navigation system.

3. The method of claim 1, wherein the at least one instrument is a retractor.

4. The method of claim 1, wherein the at least one instrument is at least one of a port and a tubular retractor.

5. The method of claim 1, further comprising:
receiving information about a surgical operating room, wherein the information is at least one of an image, sensor data, electro-magnetic data, or Lidar data;
identifying one or more obstacles in the information about the surgical operating room; and
defining the one or more no-fly zones based on the identified one or more obstacles.

6. The method of claim 5, wherein defining the one or more no-fly zones comprises determining an outer boundary of one or more objects.

7. The method of claim 1, wherein calculating the path is further based on one or more parameters and wherein the method further comprises assigning a weight to each parameter of the one or more parameters.

8. The method of claim 7, wherein artificial intelligence uses one or more data models to assign the weight.

9. The method of claim 1, further comprising:
receiving updated information about an updated position of the at least one instrument;
calculating at least one of an updated void volume and an updated position of the void volume based on the updated position of the at least one instrument; and
updating the updated work volume based on at least one of the updated void volume and the updated position of the void volume.

10. The method of claim 1, further comprising:
causing the robotic arm to move along the path.

11. The method of claim 1, further comprising:
determining a cut angle to a target anatomical element based on avoiding the one or more no-fly zones, wherein calculating the path is further based on the determined cut angle.

12. The method of claim 1, wherein the one or more no-fly zone includes the at least one instrument.

13. A device for planning a path comprising:
at least one processor; and
a memory storing data for processing by the at least one processor that, when processed, the data causes the at least one processor to:
map a work volume and one or more no-fly zones, the work volume defining a volume which a robot may access and each of the one or more no-fly zones defining at least one volume which the robot is restricted from accessing;
receive information about a position of at least one instrument;
receive an image of an incision;
process the image to determine dimensions of the incision based on the image;
calculate a void volume based on the position of the at least one instrument and the dimensions of the incision;
update the one or more no-fly zones to remove the void volume; and
calculate a path for a robotic arm of the robot from outside a patient anatomy to within the patient anatomy that avoids the one or more no-fly zones,
wherein calculating the void volume is further based on known dimensions of the at least one instrument obtained from measurements of the at least one instrument received from a database.

14. The device of claim 13, wherein one or more markers are affixed to the at least one instrument and the information about the position of the at least one instrument is received from a navigation camera configured to detect the position of the one or more markers.

15. The device of claim 13, wherein the memory stores further data for processing by the processor that, when processed, causes the processor to:
receive updated information about an updated position of the at least one instrument;
calculate at least one of an updated void volume and an updated position of the void volume based on the updated position of the at least one instrument; and
update the work volume based on at least one of the updated void volume and the updated position of the void volume.

16. A system for orienting a robotic arm comprising:
a robotic arm;
at least one processor; and
a memory storing data for processing by the at least one processor that, when processed, the data causes the at least one processor to:
map a work volume and one or more no-fly zones, the work volume defining a volume which the robotic arm may access and each of the one or more no-fly zones defining at least one volume which the robotic arm is restricted from accessing;
receive information about a position of at least one instrument;
receive an image of an incision;
process the image to determine dimensions of the incision based on the image;
calculate a void volume based on the position of the at least one instrument and the dimensions of the incision;
update the work volume to include the void volume to yield an updated work volume;
calculate a path for the robotic arm from outside a patient anatomy to within the patient anatomy based on the updated work volume and that avoids the one or more no-fly zones; and
cause the robotic arm to move along the path,
wherein calculating the void volume is further based on known dimensions of the at least one instrument obtained from measurements of the at least one instrument received from a database.

* * * * *